US009375354B2

(12) United States Patent
Lenser et al.

(10) Patent No.: US 9,375,354 B2
(45) Date of Patent: Jun. 28, 2016

(54) METHODS AND APPARATUSES FOR CONVEYING ABSORBENT ARTICLES IN A CONVERTING LINE

(75) Inventors: Todd Douglas Lenser, Liberty Township, OH (US); Uwe Schneider, Cincinnati, OH (US); David Carlton Ordway, Oxford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 754 days.

(21) Appl. No.: 13/616,478

(22) Filed: Sep. 14, 2012

(65) Prior Publication Data

US 2014/0080692 A1    Mar. 20, 2014

(51) Int. Cl.
| | |
|---|---|
| *B32B 38/04* | (2006.01) |
| *B65H 45/08* | (2006.01) |
| *B65H 20/02* | (2006.01) |
| *B65H 20/06* | (2006.01) |

(Continued)

(52) U.S. Cl.
CPC ..... *A61F 13/15764* (2013.01); *A61F 13/15804* (2013.01); *B65H 20/06* (2013.01); *B29C 2793/009* (2013.01); *B29C 2793/0027* (2013.01); *B32B 38/0004* (2013.01); *B32B 38/10* (2013.01); *B65H 45/08* (2013.01); *B65H 45/22* (2013.01); *B65H 45/28* (2013.01); *B65H 2404/1122* (2013.01); *B65H 2404/25* (2013.01); *B65H 2404/261* (2013.01); *B65H 2511/13* (2013.01); *B65H 2701/1125* (2013.01); *B65H 2801/57* (2013.01); *Y10T 156/10* (2015.01); *Y10T 156/1049* (2015.01)

(58) Field of Classification Search
CPC ............... B65H 2404/1121; B65H 2404/1122; B65H 2404/261; B65H 45/08; B65H 45/22; B65H 45/28; B65H 2301/20; Y10T 156/1049; Y10T 156/10; A61F 13/15764; A61F 13/15804; B29C 2793/0027; B29C 2793/009; B32B 38/0004; B32B 38/04; B32B 38/045; B32B 38/10

See application file for complete search history.

(56) References Cited

U.S. PATENT DOCUMENTS

| | | |
|---|---|---|
| 3,860,003 A | 1/1975 | Buell |
| 4,610,678 A | 9/1986 | Weisman et al. |

(Continued)

FOREIGN PATENT DOCUMENTS

JP       64-034854 A       7/1987

OTHER PUBLICATIONS

PCT International Search Report PCT/US2013/058899, dated Feb. 11, 2014, 8 pages.

*Primary Examiner* — Linda L Gray
(74) *Attorney, Agent, or Firm* — Charles R. Matson

(57) ABSTRACT

The apparatuses and methods herein may be configured to transport articles in the form of continuous lengths of substrates having thicknesses that varies along a machine direction and/or cross direction. The conveyance apparatuses may be configured to include a first carrier and second carrier, wherein each carrier includes an endless belt positioned adjacent to the other so as to define a nip region between the endless belts, the nip region extending in a machine direction and a cross direction. The carriers may also include compliant rollers in rolling contact with the endless belts. Each compliant roller may be elastomeric and adapted to provide a reaction force normal to the endless belt along the machine and/or cross direction of the nip region. As such, the compliant rollers help maintain and hold the endless belts in contact with both relatively thin and thick areas of the substrate advancing through the nip region.

8 Claims, 12 Drawing Sheets

(51) Int. Cl.
   *A61F 13/15*   (2006.01)
   *B65H 45/28*   (2006.01)
   *B32B 38/00*   (2006.01)
   *B32B 38/10*   (2006.01)
   *B65H 45/22*   (2006.01)

(56) References Cited

U.S. PATENT DOCUMENTS

| | | |
|---|---|---|
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,562,646 A | 10/1996 | Goldman et al. |
| 5,599,335 A | 2/1997 | Goldman et al. |
| 5,628,097 A | 5/1997 | Benson et al. |
| 5,669,894 A | 9/1997 | Goldman et al. |
| 5,745,922 A | 5/1998 | Rajala et al. |
| 5,916,661 A | 6/1999 | Benson et al. |
| 6,107,539 A | 8/2000 | Palumbo et al. |
| 6,248,195 B1 | 6/2001 | Schmitz |
| 6,545,197 B1 | 4/2003 | Miller et al. |
| 6,546,987 B1 | 4/2003 | Tachibana et al. |
| 6,564,928 B1 * | 5/2003 | Darrou et al. ............... 198/626.1 |
| 6,790,798 B1 | 9/2004 | Suzuki et al. |
| 7,383,865 B2 | 6/2008 | Umebayashi et al. |
| 7,569,039 B2 | 8/2009 | Matsuda et al. |
| 2004/0097895 A1 | 5/2004 | Busam et al. |
| 2004/0158212 A1 | 8/2004 | Ponomarenko et al. |
| 2005/0107764 A1 | 5/2005 | Matsuda et al. |
| 2007/0219521 A1 | 9/2007 | Hird et al. |
| 2008/0315512 A1 * | 12/2008 | Naruoka et al. ......... 271/265.01 |
| 2009/0312730 A1 | 12/2009 | LaVon et al. |
| 2010/0032263 A1 | 2/2010 | Yamamoto |
| 2010/0263987 A1 | 10/2010 | Meyer et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |
| 2012/0021186 A1 | 1/2012 | Schneider |
| 2012/0061015 A1 | 3/2012 | LaVon et al. |
| 2012/0061016 A1 | 3/2012 | LaVon et al. |

* cited by examiner

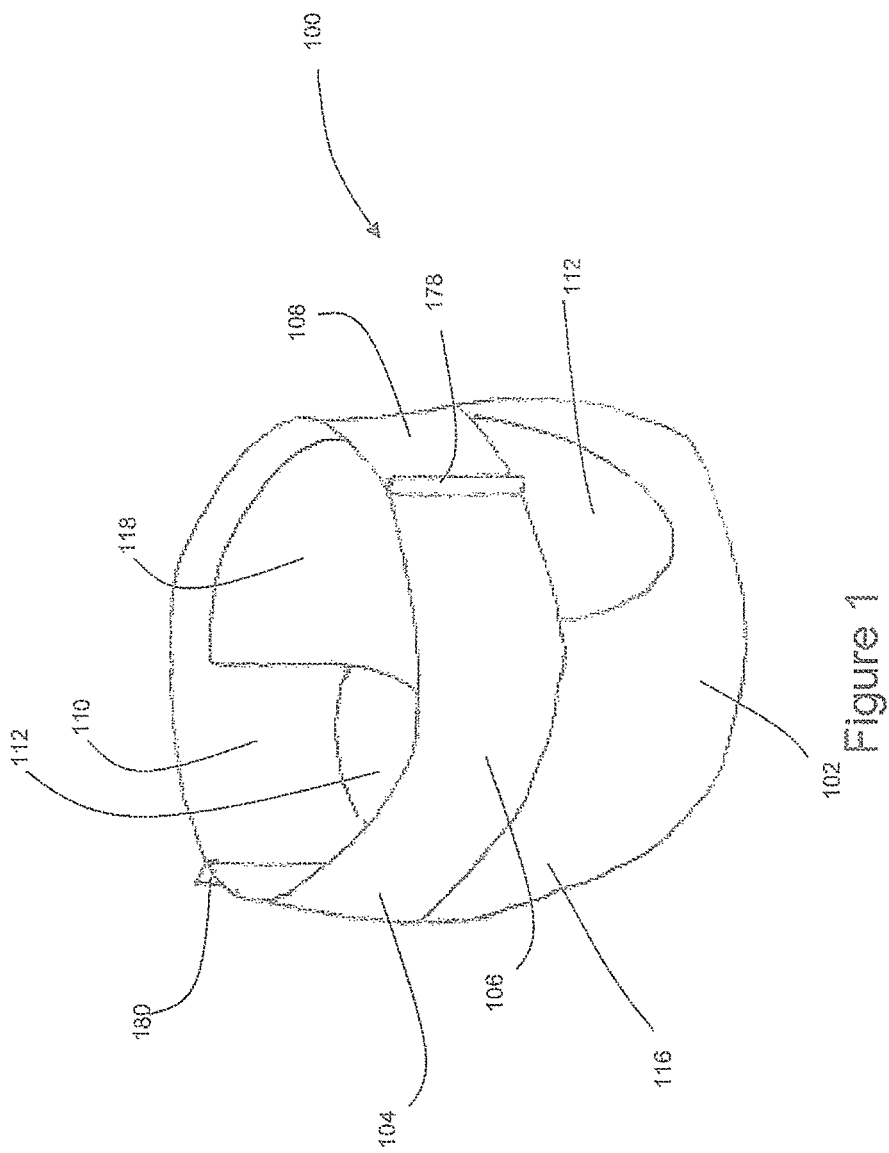

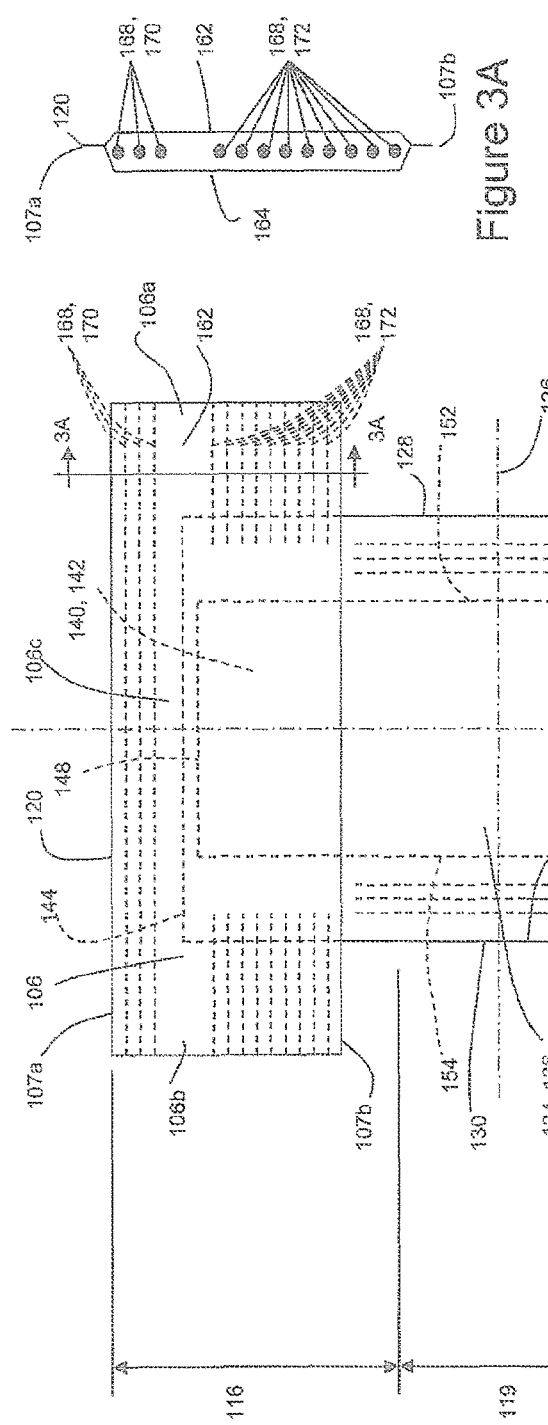
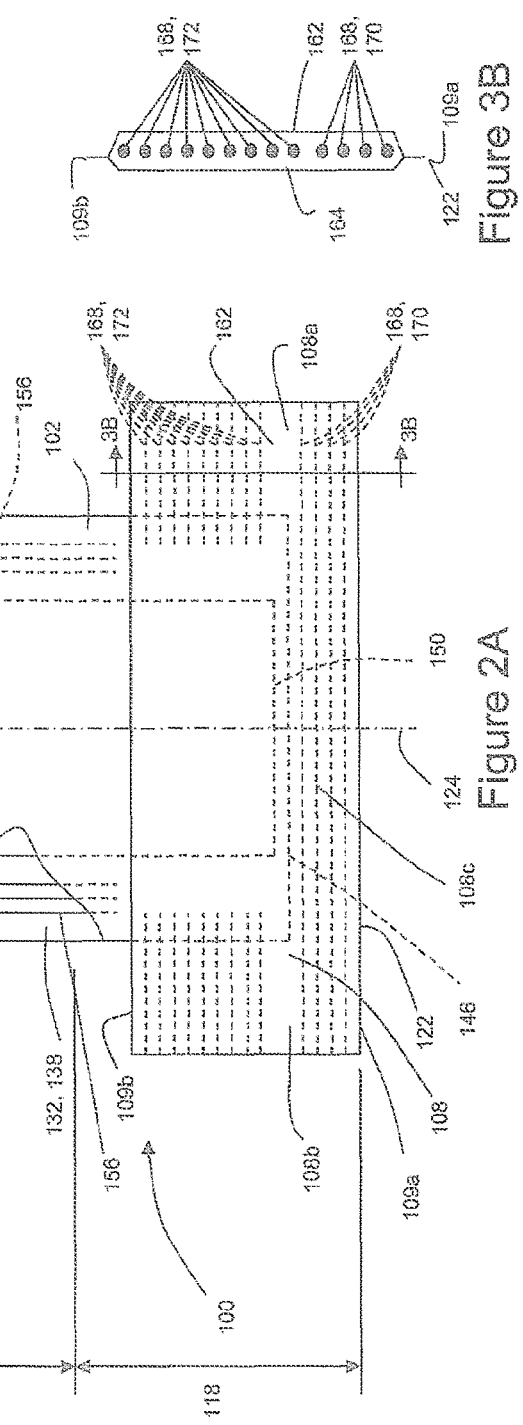

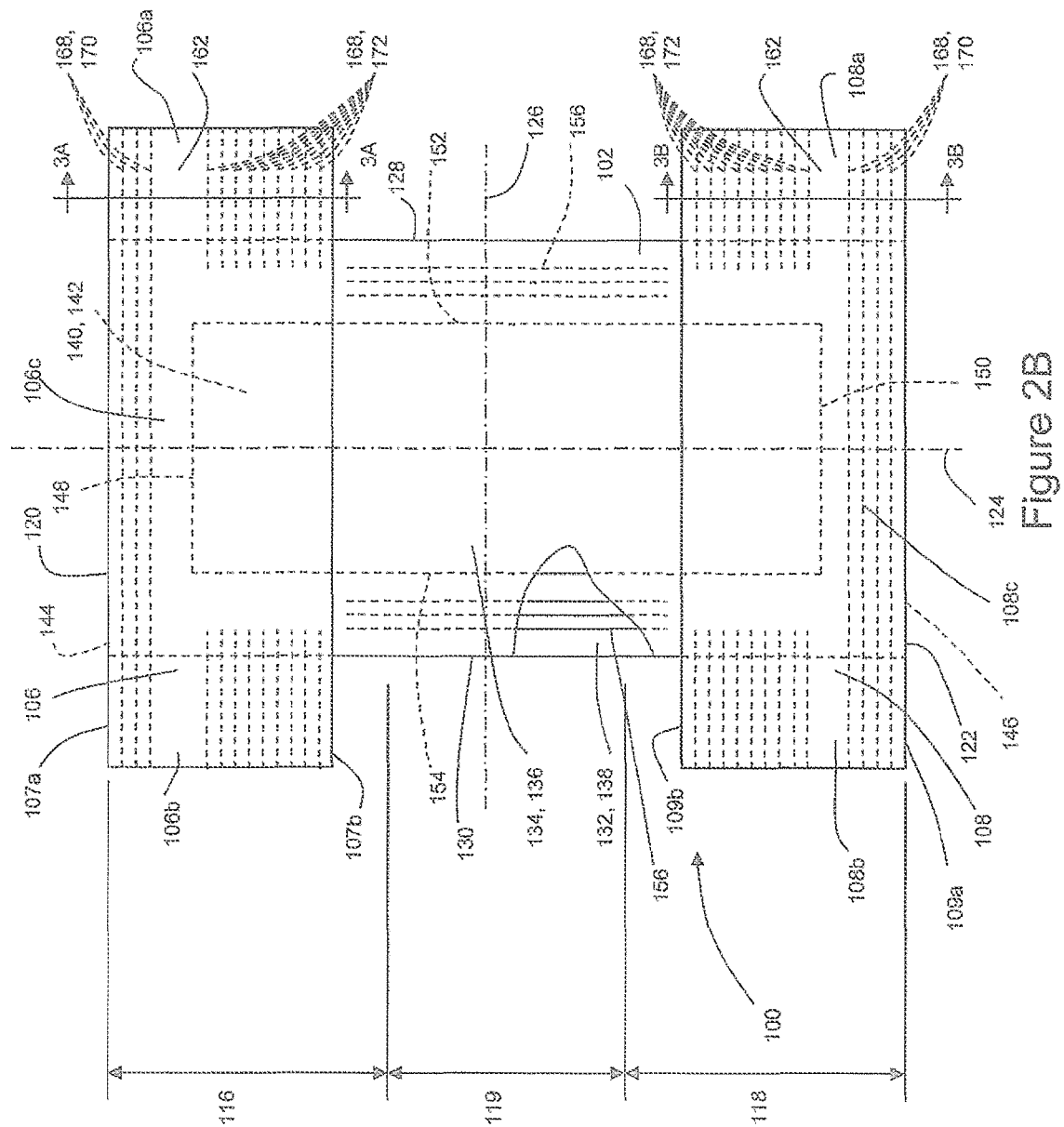

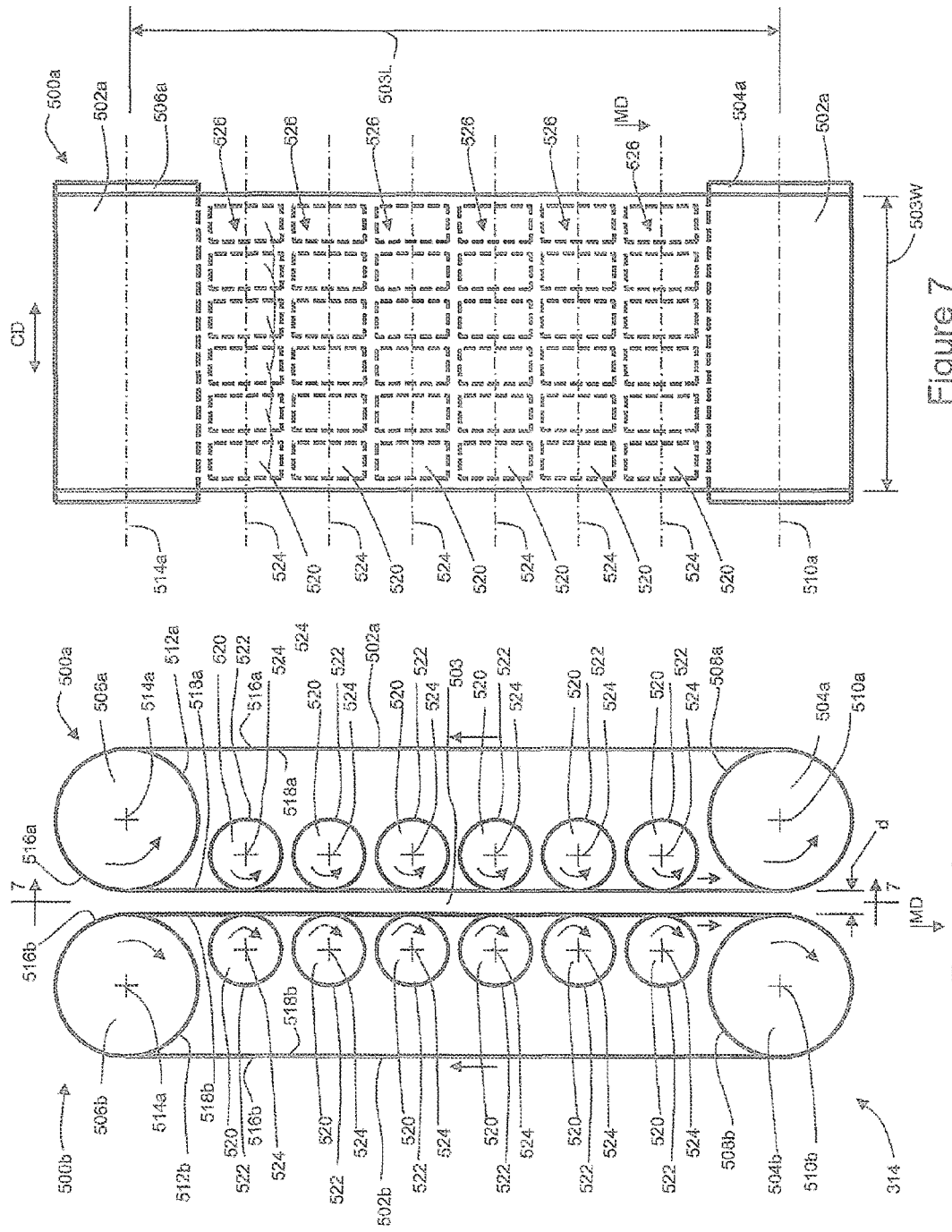

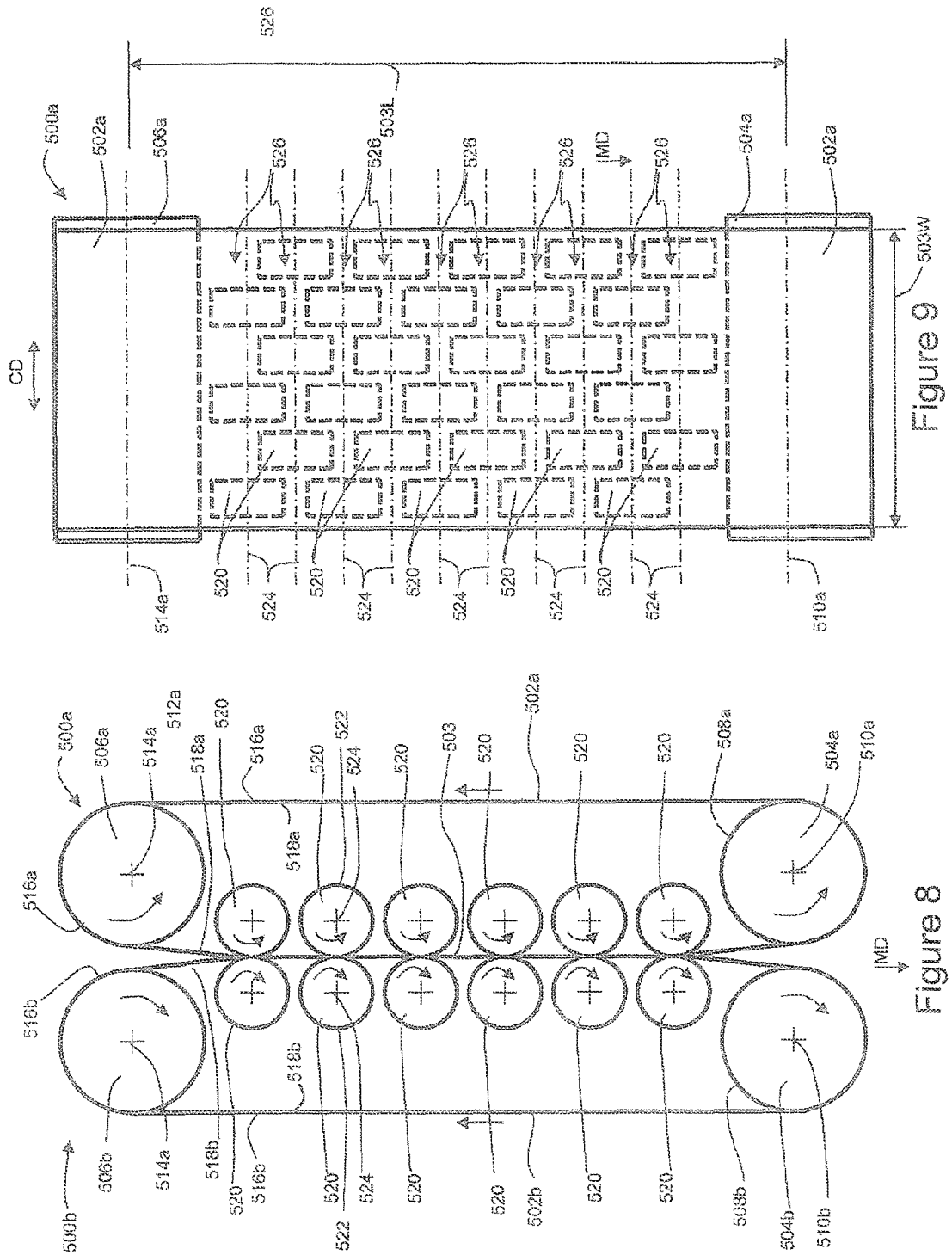

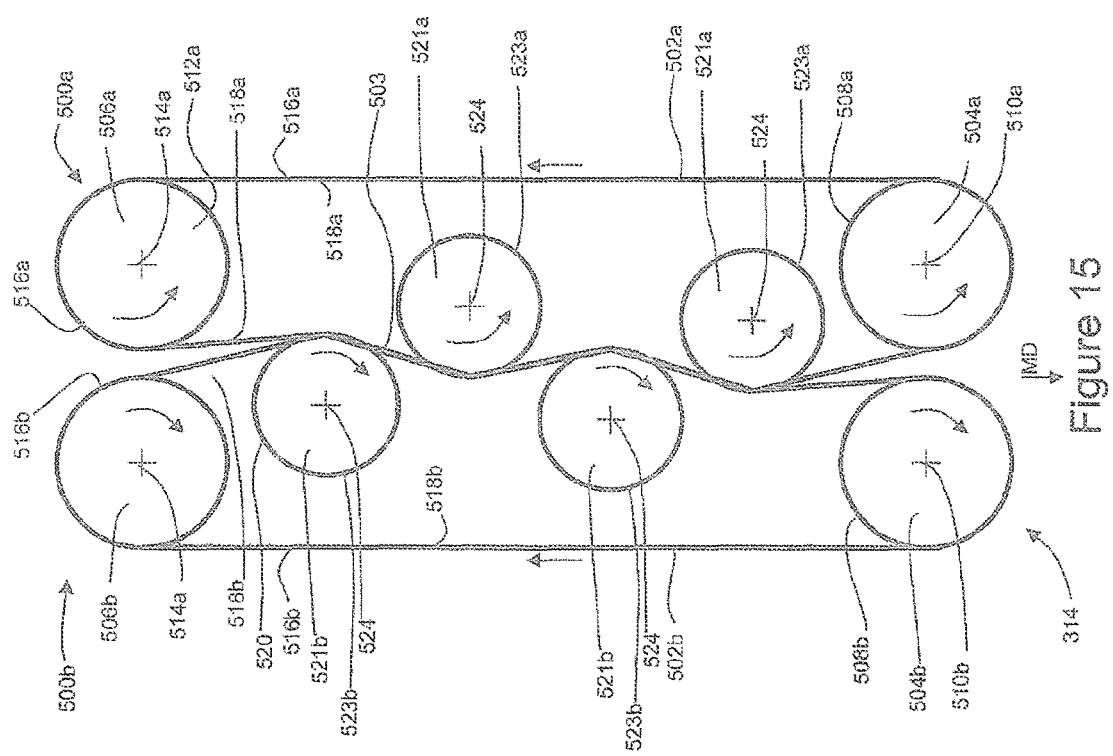

METHODS AND APPARATUSES FOR CONVEYING ABSORBENT ARTICLES IN A CONVERTING LINE

FIELD OF THE INVENTION

The present disclosure relates to systems and methods for manufacturing disposable absorbent articles, and more particularly, systems and methods for conveying absorbent articles through a converting line.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

In converting processes, various conveyors may be used for advancing continuous lengths of flexible substrates and/or absorbent articles. In some instances, there is a need to transport a flexible product, such as a continuous length of assembled disposable absorbent articles, from one unit operation to another unit operation. For example, conveyors may be configured to convey a continuous length of absorbent articles from a folding unit to a rotary cutting knife. As such, an upstream conveyor may transport the continuous length of absorbent articles to the rotary knife, and a downstream conveyor may transport discrete absorbent articles from the rotary knife. With rotary knives, the flexible absorbent articles cannot be pulled from the discharge side of the knife for at least one part of the machine cycle, and as such, the upstream conveyor may need to push the absorbent articles for a portion of the machine cycle. Various types of conveyors may be used to carry out these types of functions, such as for example: a set of opposed rollers; opposed conveyors; or vacuum conveyors. However, these conveyor apparatuses may not account for differences in thickness of the flexible absorbent articles, and as such, may have some drawbacks. For example, opposed conveyors may be positioned to have a nip with a relatively large gap, and may only grip the flexible product in regions having relatively large thicknesses. Thus, such conveyors may have not be able to adequately hold the flexible absorbent articles during portions of the machine cycle when it is necessary to push the absorbent articles downstream. In sections where the flexible product is thin, upstream web tension can pull the flexible product out of the nip point between the conveyors. Consequently, the flexible product may not be transported into the downstream unit operation, resulting in a jam and line shutdown.

Consequently, it would be beneficial to provide a relatively less complex apparatus and method for conveying a continuous length of absorbent articles that utilizes compliant rollers to transport the web that also account for variations in thickness of a product web.

SUMMARY OF THE INVENTION

The apparatuses and methods herein may be configured to transport articles in the form of continuous lengths of substrates having thicknesses that varies along a machine direction and/or cross direction. The conveyance apparatuses may be configured to include a first carrier and second carrier, wherein each carrier includes an endless belt positioned adjacent to the other so as to define a nip region between the endless belts, the nip region extending in a machine direction and a cross direction. The carriers may also include compliant rollers in rolling contact with the endless belts. Each compliant roller may be elastomeric and adapted to provide a reaction force normal to the endless belt along the machine and/or cross direction of the nip region. As such, the compliant rollers help maintain and hold the endless belts in contact with both relatively thin and thick areas of the substrate advancing through the nip region.

In one form, a method for conveying articles in a web converting process comprises the steps of: providing a first carrier including a first plurality of rollers in rolling contact with a first endless belt; providing a second carrier including a second plurality of rollers in rolling contact with a second endless belt, wherein the first carrier is positioned adjacent the second carrier to define a nip region between the first endless belt and the second endless belt, the nip region having a length extending in a machine direction and a width extending in a cross direction; advancing a plurality of articles in the machine direction through the nip region, each article having a varying thickness along the machine direction and the cross direction; varying a distance between the first belt and the second belt along the machine direction and cross direction of the nip to conform with the varying thickness of the articles by deforming at least one of the first plurality of rollers.

In another form, an apparatus for conveying absorbent articles comprises: a first carrier comprising: a first endless belt having a first surface and an opposing second surface; a first plurality of compliant rollers, each compliant roller having a hub member, a rim member surrounding the hub member, and an intermediate member connecting the hub member with the rim member; and wherein the rims of the first plurality of rollers are in rolling contact with the second surface of the first endless belt; a second carrier comprising a second endless belt having a first surface and an opposing second surface; and wherein the first carrier is positioned adjacent the second carrier to define a nip region between first surface of the first endless belt and the first surface of the second endless belt, the nip region having a length extending in a machine direction and a width extending in a cross direction.

BRIEF DESCRIPTION OF THE DRAWINGS

FIG. 1 is a perspective view of a diaper pant.

FIG. 2A is a partially cut away plan view of the diaper pant shown in FIG. 1.

FIG. 2B is a partially cut away plan view of a second embodiment of a diaper pant.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 6 is a detailed schematic view of an embodiment of a compliant conveyance apparatus including a first carrier and a second carrier apparatus.

FIG. 7 is a plan view of the first carrier from FIG. 6 taken along line 7-7.

FIG. 8 is a detailed schematic view of a second embodiment of a compliant conveyance apparatus including a first carrier and a second carrier apparatus.

FIG. 9 is a plan view of a second embodiment of the first carrier apparatus.

FIG. 15 is a side view of a third embodiment of a compliant conveyance apparatus.

DETAILED DESCRIPTION OF THE INVENTION

Figure 4:
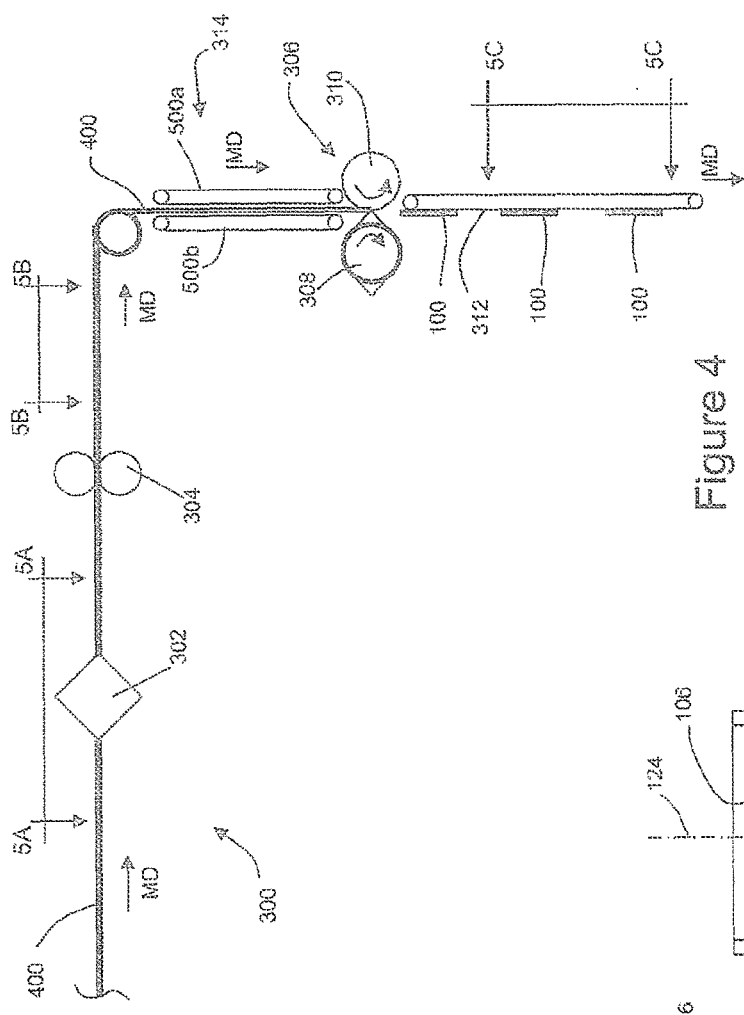
FIG. 4 is a schematic side view of a converting apparatus adapted to manufacture diapers including a compliant conveyance apparatus.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a defined woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

The present disclosure relates to methods and apparatuses for manufacturing absorbent articles, and more particularly, systems and methods for conveying absorbent articles along a converting line. More specifically, apparatuses and methods according to the present disclosure may be configured to transport or advance articles in the form of continuous lengths of substrates having a thickness that varies along a machine direction and/or cross direction. As discussed in more detail below, the conveyance apparatuses and methods may be configured to include a first carrier and second carrier, wherein each carrier includes an endless belt. The first and second carriers are positioned adjacent to each other so as to define a nip region between the endless belts, the nip region extending in a machine direction and a cross direction. The first and/or second carrier may also include compliant rollers in rolling contact with the endless belt. Each compliant roller may be elastomeric and adapted to provide a reaction force normal to the endless belt along the machine and/or cross direction of the nip region. Thus, as a substrate advances through the nip region, the compliant rollers force the endless belt against the substrate to compress the substrate between the endless belts of the first and second carriers in the nip region. The compliant rollers also allow the endless belt to deflect by different amounts in the nip region in accordance with the varying thicknesses of the substrate advancing through the nip region. As such, the compliant rollers help maintain and hold the endless belts in contact with and compression forces on both relatively thin and relatively thick areas of the substrate advancing through the nip region.

It is to be appreciated that although the methods and apparatuses herein may be configured to convey various types of products, the methods and apparatuses herein are discussed below in the context of manufacturing absorbent articles. In particular, the methods and apparatuses are discussed in the context of conveying diapers during production.

FIGS. 1 and 2A show an example of a diaper pant 100 that may be assembled and conveyed in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 120 in the front waist region 116 and a longitudinally opposing and laterally extending back waist edge 122 in the back waist region 118.

To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 120 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 120 in the front waist region 116 and the laterally extending back waist edge 122 in the back waist region 118. When the diaper pant 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is also to be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562, 646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795, 454; and 4,704,115; and U.S. Patent Publication No. 2009/ 0312730A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172.

As shown in FIG. 2A, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2A, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

As previously mentioned, the conveyance methods and systems according to the present disclosure may be utilized during the assembly of various components of absorbent articles, such as diapers 100. During the assembly process, various continuous substrates and/or discrete components may be combined with each other to form a continuous length of absorbent articles. At a downstream portion of the converting process, the continuous length of absorbent articles may be folded, seamed, subjected to a final knife, and cut to create separate and discrete absorbent articles in the form of diapers. The discrete absorbent articles may then advance in a machine direction MD and subject to further processing steps, such as for example, side panel tucking and packaging operations. As discussed in more detail below, converting apparatuses may include compliant conveyance apparatuses that are configured to advance a continuous length of absorbent articles from a first unit operation, such as a seaming apparatus, to a second unit operation, such as a cutting apparatus that cuts the continuous length of absorbent articles into discrete absorbent articles. Such compliant conveyance apparatuses may be configured to account for differences in the thickness of the continuous length of absorbent articles.

FIG. 4 shows an example converting apparatus 300 adapted to manufacture diaper pants 100 and that may operate in conjunction with a compliant conveyance apparatus. The method of operation of the converting apparatus 300 may be described with reference to the various components of pant diapers 100 described above and shown in FIGS. 1 and 2A. Although the following methods are provided in the context of the diaper 100 shown in FIGS. 1 and 2A, it is to be appreciated that various embodiments of diapers can be manufactured according to the methods disclosed herein, such as for example, the absorbent articles disclosed in U.S. Pat. Nos. 7,569,039 and 5,745,922; U.S. Patent Publication Nos. 2005/0107764A1, 2012/0061016A1, and 2012/0061015A1, which are all hereby incorporated by reference herein.

As shown in FIG. 4, the converting apparatus operates to advance a continuous length of absorbent articles 400 including discrete chassis 102 connected with continuous lengths of advancing first and second elastic belt substrates 402, 404 along a machine direction MD. As discussed in more detail below, portions of the first belt substrate may be converted to correspond with the first elastic belt 106 and portions of the second belt substrate may be converted to correspond with the second elastic belt 108 discussed above with reference to FIGS. 1-3B. As shown in FIGS. 4 and 5A, the first belt substrate 402 includes a first, garment facing, surface 402a and an opposing second, wearer facing, surface 402b. And the second belt substrate 404 a first, garment facing, surface 404a and an opposing second, wearer facing, surface 404b. The lateral axis of each chassis 102 is parallel with the machine direction MD, and the longitudinal axis of each chassis is perpendicular with the machine direction MD. The chassis 102 are also spaced apart from each other along the machine direction. Opposing waist regions 116, 118 of the spaced apart chassis 102 are connected with continuous lengths of advancing first and second elastic belt substrates 402, 404.

It is to be appreciated that FIG. 4 illustrates an example a downstream portion of a converting process configured to assemble a continuous length of absorbent articles by combining various continuous substrates and/or discrete components with each other. It is to be appreciated the apparatus of FIG. 4 can be configured to work with various configurations of converting systems, such as for example those disclosed in U.S. patent application Ser. No. 13/434,984, entitled "Apparatuses and Methods for Making Absorbent Articles," filed on Mar. 30, 2012.

As shown in FIGS. 4 and 5A, the continuous length of absorbent articles 400 advances to a folding apparatus 302. At the folding apparatus 302, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis 102 also positions the wearer facing surface 402b of the first belt substrate 402 extending between each chassis 102 in a facing relationship with the wearer facing surface 404b of the second belt substrate 404 extending between each chassis 102.

Figure 5C:
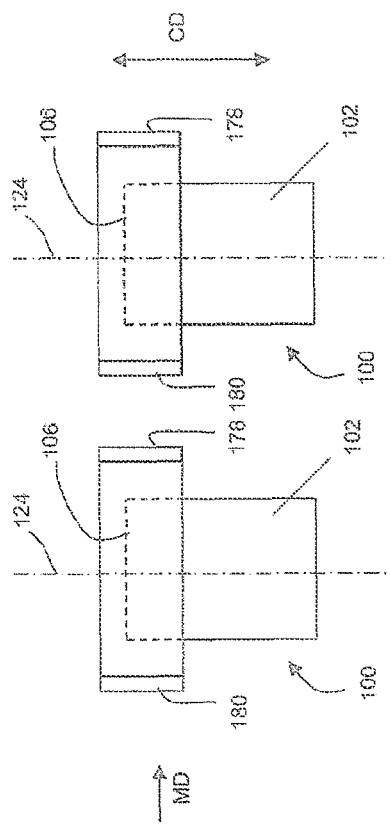
FIG. 5C is a view of two discrete absorbent articles oriented such that the longitudinal axis is generally perpendicular to the machine direction MD from FIG. 4 taken along line 5C-5C.
Figure 5A:
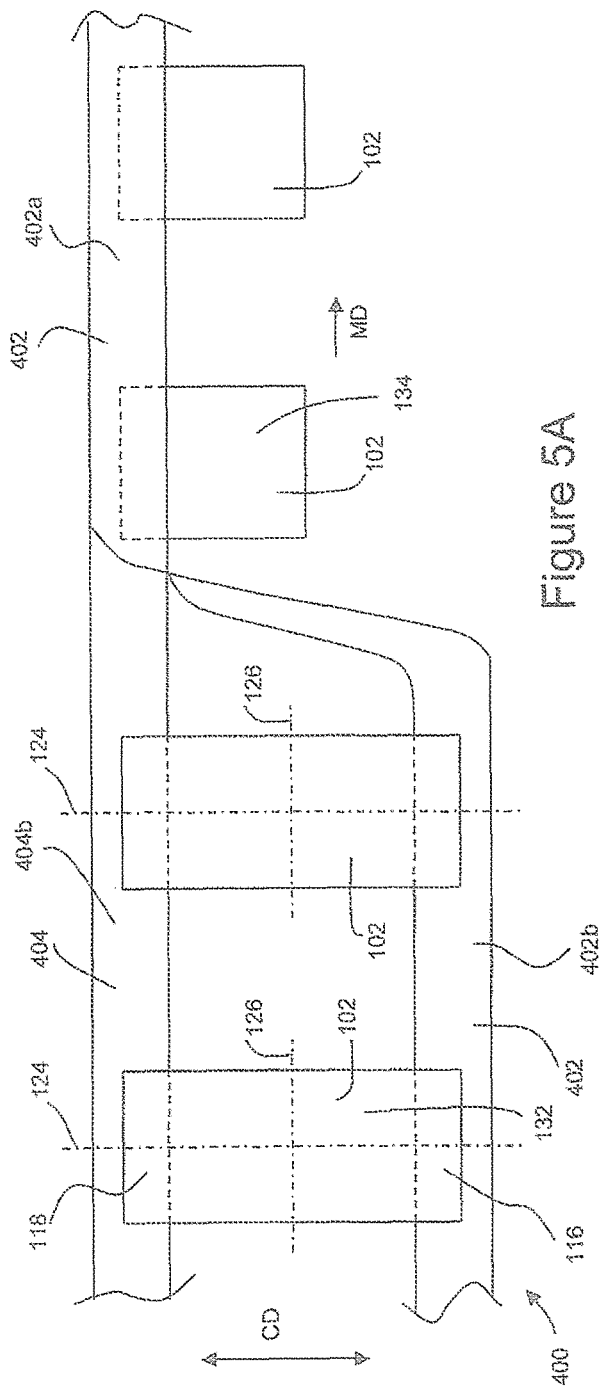
FIG. 5A is a view of multiple discrete chassis connected with front and back side panel material and being folded to place the front and back side panel material in a facing relationship from FIG. 4 taken along line 5A-5A.
Figure 5B:
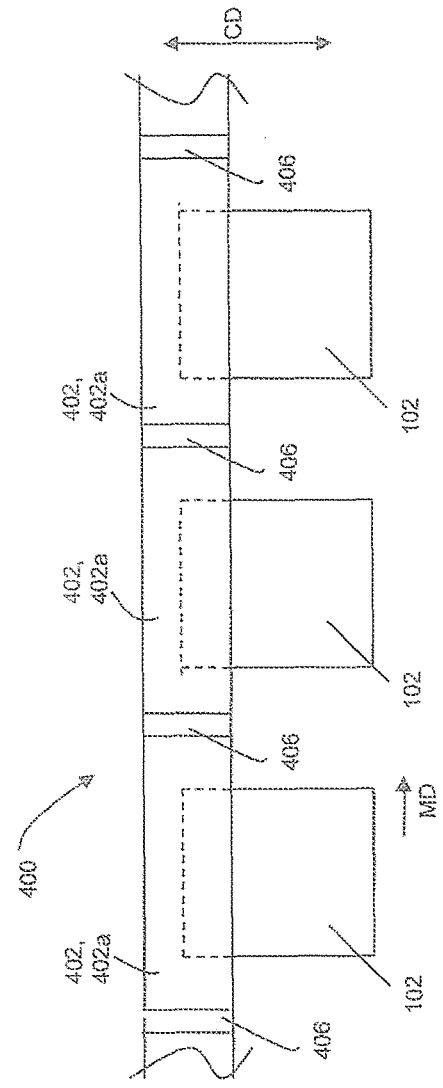
FIG. 5B is a view of folded multiple discrete chassis with the front and back side panel material in a facing relationship from FIG. 4 taken along line 5B-5B.

As shown in FIGS. 4 and 5B, the folded discrete chassis 102 connected with the first and second belt substrates 402, 404 are advanced from the folding apparatus 302 to a bonder 304. The bonder 304 operates to bond a portion of the second belt substrate 404 extending between each chassis 102 with a portion of the first belt substrate 402 extending between each chassis 102, thus creating discrete bond regions 406. It is to be appreciated that various types of bonder apparatuses and methods can be used to bond the second belt substrate material 404 with the first belt substrate material 402, such as for example disclosed in U.S. Pat. Nos. 6,248,195; 6,546,987; and 7,383,865, as well as U.S. Patent Publication No. 2012/0021186A1, which are incorporated by reference herein. With continued reference to FIG. 4, the continuous length of absorbent articles 400 are advanced from the bonder 304 to a cutting apparatus 306 including a knife roll 308 and anvil roll 310. The cutting apparatus 306 cuts the discrete bond regions 406 along the cross direction CD to create a first side seam 178 on an absorbent article 100 and a second side seam 180 on a subsequently advancing absorbent article. As such, the elastic belt substrates 402, 404 are cut along the seams 406 to create discrete diapers 100, such as shown in FIG. 1. From the cutting apparatus 306, a carrier 312 may advance the discrete diapers 100 in the machine direction MD to further unit operations, such side panel tucking and packaging operations. It is to be appreciated that the carrier 312 may be configured in various ways. For example, the carrier 312 may include one or more conveyor belts or a vacuum drum.

As shown in FIG. 4, the apparatus 300 may include a compliant conveyance apparatus 314 that conveys and holds the continuous length of absorbent articles 400 in position while advancing to the cutting apparatus 306. As shown in FIG. 4, the compliant conveying apparatus may include a first carrier 500a and a second carrier 500b. The first carrier 500a includes a first endless belt 502a, and the second carrier 500b includes a second endless belt 502b. As discussed in more detail below, the first carrier 500a is positioned adjacent to the second carrier 500b to define a nip region 503 between the first endless belt 502a and the second endless belt 502b. The nip region 503 may extend in the machine direction MD and the cross direction CD and may correspond with the region wherein the first and second endless belts 502a, 502b are closest to each other. For example, as shown in FIGS. 6 and 7, the endless belts 502a, 502b are separated by a minimum distance, d, in the nip region. Thus, the nip region 503 may define a width 503W in cross direction and a length 503L in the machine direction. And the width 503W of the nip region 503 may correspond with the cross direction CD width of the endless belts 502a, 502b, and the length 503L of the nip region 503 may correspond with the machine direction MD length of the belts 502a, 502b that are separated by distance, d. It is to be appreciated that in some configurations, the first and second carriers 500a, 500b are positioned adjacent to each other such that the first and second endless belts 502a, 502b, are in contact with each other in the nip region 503, such as shown in FIG. 8. As such, the distance, d, in FIG. 8 is zero. The first and second carriers 500a, 500b may also be positioned adjacent to each other so as to define a distance, d, of zero, and may also be "pre-loaded" wherein the compliant rollers discussed below exert forces on the endless belts 502a, 502b toward each other in the nip region 503.

As shown in FIG. 5, the first endless belt 502a surrounds a first drive roller 504a and a first idler roller 506a. The first drive roller 504a defines an outer circumferential surface 508a and is adapted to rotate around an axis of rotation 510a, and the first idler roller defines 506a an outer circumferential surface 512a and is adapted to rotate around an axis of rotation 514a. The first endless belt 502a includes a first surface 516a and an opposing second surface 518a, wherein the second surface 518a is in contact with the outer circumferential surfaces 508a, 512a of the first drive roller 504a and the first idler roller 506a. As such, when the first drive roller 504a and the first idler roller 506a rotate around the axes of rotation 510a, 514a in the direction shown in FIG. 5, the first surface 516a of the first endless belt 502a advances in the machine direction MD through the nip region 503.

With continued reference to FIG. 5, the second endless belt 502b surrounds a second drive roller 504b and a second idler roller 506b. The second drive roller 504b defines an outer circumferential surface 508b and is adapted to rotate around an axis of rotation 510b, and the second idler roller defines 506b an outer circumferential surface 512b and is adapted to rotate around an axis of rotation 514b. The second endless belt 502b includes a first surface 516b and an opposing second surface 518b, wherein the second surface 518b is in contact with the outer circumferential surfaces 508b, 512b of the second drive roller 504b and the second idler roller 506b. As such, when the second drive roller 504b and the second idler roller 506b rotate around the axes of rotation 510b, 514b in the direction shown in FIG. 5, the first surface 516b of the second endless belt 502b advances in the machine direction MD through the nip region 503.

As previously mentioned, the first 500a and/or second carrier 500b may also include compliant rollers 520 that allow the endless belts 502a, 502b to deflect away from each other by different amounts in the nip region 503 in accordance with the varying thicknesses of the substrate advancing through the nip region 503. For example, as shown in FIGS. 5 and 6, the first carrier 500a and the second 500b may include compliant rollers 520 positioned in rolling contact with the first and second endless belts 502a, 502b in the nip region 503. More particularly, each compliant roller 520 may include an outer circumferential surface 522 and may be adapted to rotate around an axis of rotation 524. As such, the outer circumferential surface 522 of the compliant rollers 520 of the first carrier 500a may be in rolling contact with the second surface 518a of the first endless belt 502a in the nip region 503. And the outer circumferential surface 522 of the compliant rollers 520 of the second carrier 500b may be in rolling contact with the second surface 518b of the second endless belt 502b in the nip region 503.

It is to be appreciated that the compliant rollers may be arranged in various configurations in the nip region 503. For example, as shown in FIG. 7, one or more compliant rollers 520 may be aligned in the cross direction CD along respective axes 524 to define a plurality of rows 526 of compliant rollers 520 arranged in the machine direction MD of the nip region 503. Although the carrier configuration shown in FIG. 7 shows six rows 526 of compliant rollers 520 it is to be appreciated that carriers may include more or less than six rows 526 of compliant rollers. In addition, although the carrier configuration shown in FIG. 7 shows six compliant rollers 520 in each row 526, it is to be appreciated that rows 526 may be configured with one or more rollers 520. Further, although FIG. 7 shows the rows 526 of the compliant rollers 520 being spaced apart from each other along the machine direction MD, it is to be appreciated that the rows 526 of compliant rollers 520 may be configured to overlap each other in the machine direction MD, such as shown in FIG. 9.

Figure 10B:
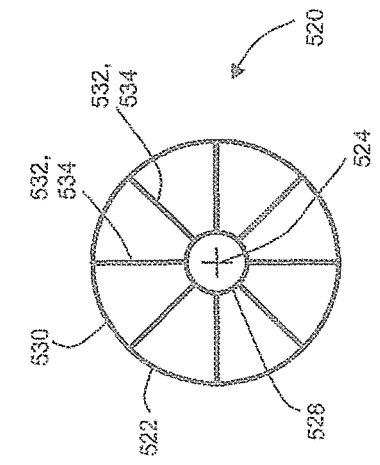
FIG. 10B is a side view of the compliant roller shown in FIG. 10A.
Figure 10A:
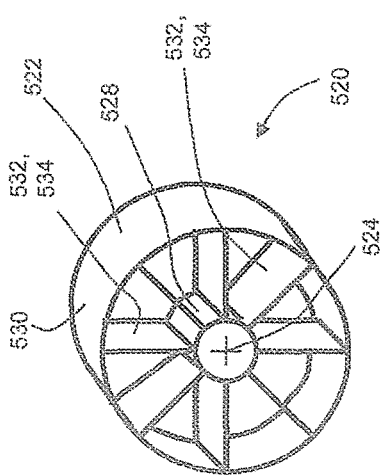
FIG. 10A is an isometric view of a compliant roller.

As mentioned above, the compliant rollers 520 are adapted to provide a reaction force normal to the endless belts 502a, 502b along the machine direction MD and/or cross direction CD of the nip region 503. It is to be appreciated that the compliant rollers 520 may be configured in various ways so as to be resiliently compressible. For example, FIGS. 10A and 10B show a compliant roller including a hub member 528, a rim member 530 surrounding the hub member 528, and an intermediate member 532 connecting the hub member 528 with the rim member 530. More particularly, the compliant roller 520 in FIGS. 10A and 10B includes a plurality of intermediate members 532 in the form of spoke members 534 extending radially outward from the hub member 528 to the rim member 530. It is to be appreciated that any portion of the compliant roller may be constructed from an elastomeric material. For example, the intermediate members 532 and/or rim member 530 may be elastomeric such that the rim member and/or intermediate members 532 may deform when subjected to radial forces.

Figure 12:
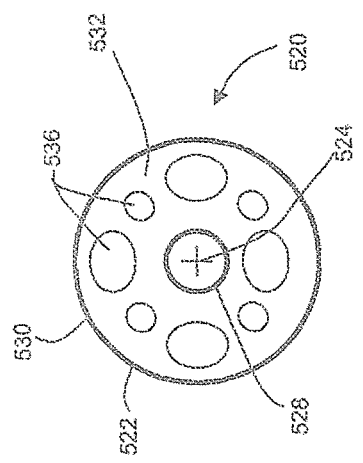
FIG. 12 is a side view of a third embodiment of a compliant roller.
Figure 11:
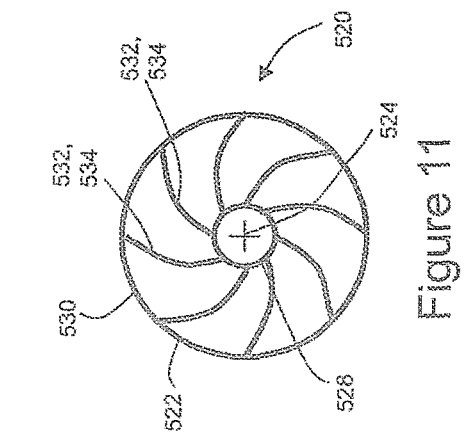
FIG. 11 is a side view of a second embodiment of a compliant roller.

Although the compliant roller 520 shown in FIGS. 10A and 10B includes eight spoke members 534, it is to be appreciated that compliant rollers may include more or less than eight spoke members 534. For example, some compliant rollers may be configured with six spoke members 534 and some compliant rollers may be configured with twelve spoke members 534. Although the compliant roller 520 shown in FIGS. 10A and 10B includes spoke members 534 that extend radially outward from the hub member along straight lines that intersect axis of rotation 524, it is to be appreciated that the spoke members 534 may be oriented in various other ways with respect to the hub member 528. In addition, the spoke members 534 may have various different shapes. For example, the compliant roller 520 shown in FIG. 11 includes curved spoke members 534. Other various types of complaint rollers 520 are available from Applied Urethane Technology, Inc. 6507 Hane Avenue, Baltimore, Md. 21237, such as for example, a three inch diameter, spiral type 65/70 shore A, white roller. It is also to be appreciated that the compliant rollers 520 may include intermediate members 532 configured as a contiguous disk-shaped member extending radially outward from the hub member 528 to the rim member 530, such as shown FIG. 12. The intermediate member 532 may also include apertures 536.

Figure 13:
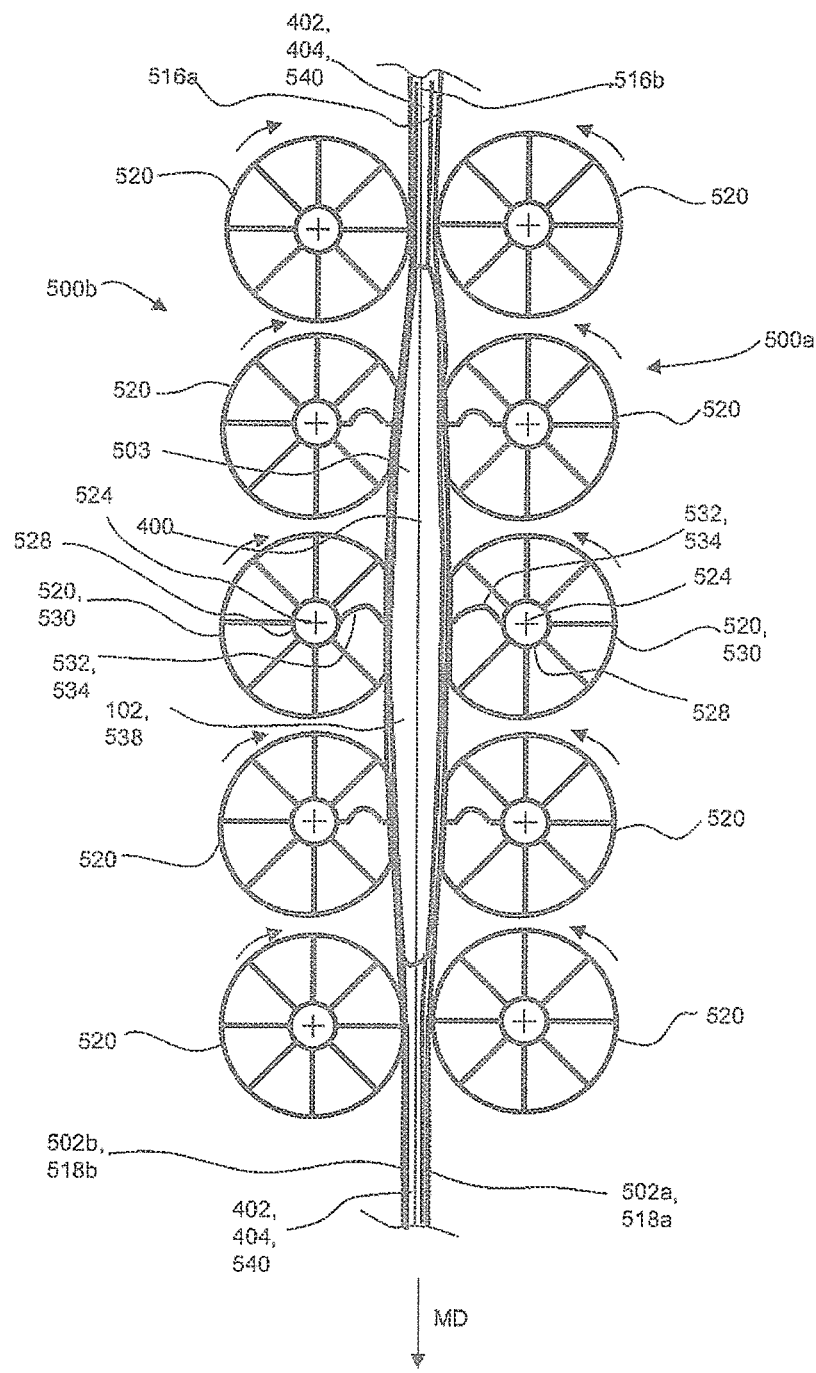
FIG. 13 is a detailed sectional view of a continuous length of absorbent articles advancing in a machine direction through a nip region between first and second carriers.
Figure 14:
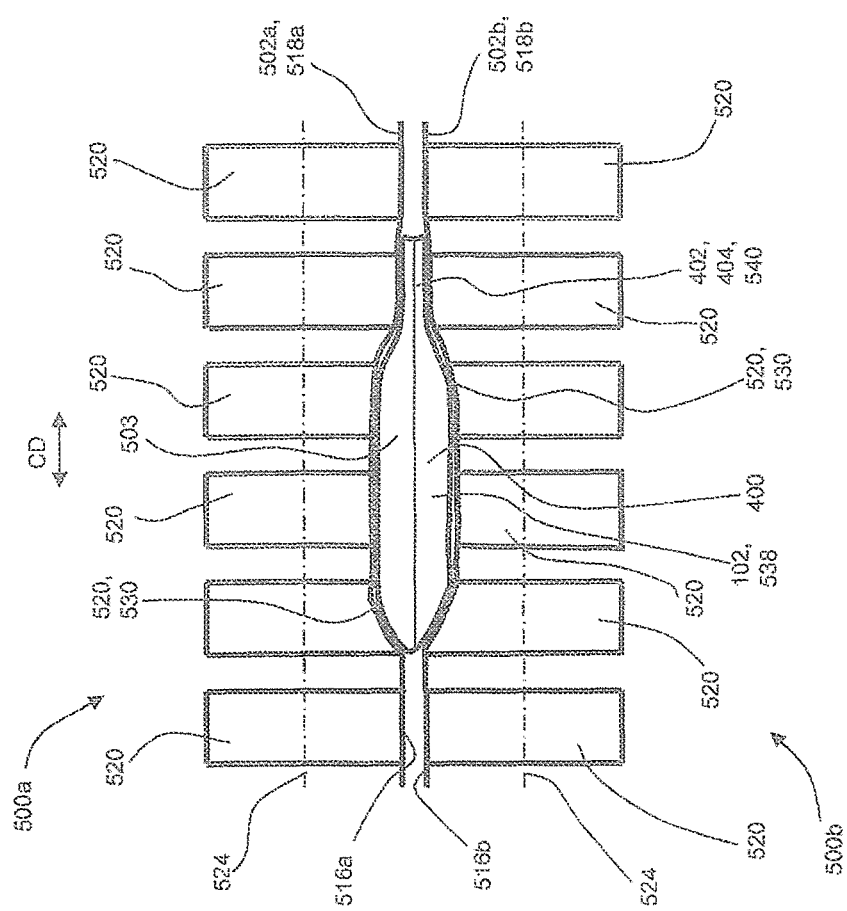
FIG. 14 is a detailed section view taken along a cross direction showing a continuous length of absorbent articles advancing through a nip region between first and second carriers.

As previously mentioned, the compliant rollers 520 allow the endless belts 502a, 502b to deflect away from each other by different amounts in the nip region 503 in accordance with the varying thicknesses of the substrate advancing through the nip region 503. At the same time, the resiliency of the compliant rollers 520 exerts opposing forces on the belts 502a, 502b toward each other to help hold the belts in contact with relatively thick and thin portions of the substrate in the nip region 503. For example, FIG. 13 shows a detailed sectional view of a continuous length of absorbent articles 400 advancing in the machine direction MD through the nip region between first and second carriers 500a, 500b. The chassis 102 may correspond with relatively thicker portions 538 of the continuous length of absorbent articles 400, and the first and second elastic belts 402, 404 in spaces between chassis 102 may correspond with relatively thinner portions of the continuous length of absorbent articles 400. As shown in FIG. 13, the relatively thicker portion of the absorbent articles 400 pushes against the first surfaces 516a, 516b of the first and second belts 502a, 502b. As such, the first belt 502a and the second belt 502b are deflected away from each other in the nip region 503. In turn, the second surfaces 518a, 518b press against the compliant rollers 520 in the nip region 503, causing the compliant rollers 520 to deform. As shown in FIG. 13, the intermediate members 532, 534 and the rim members 530 of some compliant rollers 520 are deformed and/or bent as the relatively thicker portions of the absorbent articles 400 advance through the nip region 503. Thus, the compliant rollers 520 exert reaction forces to push the endless belts 502a, 502b against the absorbent articles 400. Such reaction forces exerted by the compliant rollers 502 act to compress the absorbent articles 400 between the endless belts 502a, 502b in the nip region 503 along portions of the absorbent articles 400 having varying thicknesses. FIG. 14 also shows deflection of the belts and rollers along the cross direction CD of the nip region 503. Thus, the compliant rollers 520 are adapted to provide a reaction force normal to the endless belts 502a, 502b along the machine direction MD and/or cross direction CD of the nip region 503.

With reference back to FIG. 4, a continuous length of substrates may be in form of a continuous length of absorbent articles 400, which may be conveyed from a first unit operation, such as a seaming apparatus 304, to a second unit operation, such as a cutting apparatus 306, which may cut the continuous length of absorbent articles 400 into discrete absorbent articles 100. When advancing the continuous length of absorbent articles 400 to the cutting apparatus 306, such as a rotary cutting knife, the continuous length of absorbent articles 400 cannot be pulled from the downstream side of the cutting knife 306 for at least a portion of the machine cycle. While the articles 400 are not being pulled from the downstream side of the cutting knife 306, the conveyors 500a, 500b on the upstream side of the cutting knife 306 will push the continuous length of absorbent articles 400. As such, the conveying apparatuses 500a, 500b upstream of the cutting apparatus 306 may be configured to apply frictional forces to relatively thick portions 538 and thin portions 540 of the continuous length of articles 400, as opposed to only the relatively thick portions of the articles.

It is to be appreciated that the compliant conveyance apparatus 314 may be configured in various other ways to hold the continuous length of absorbent articles 400 in position while advancing to the cutting apparatus 306. For example, the compliant conveyance apparatus 314 in FIG. 15 includes a first carrier 500a including a first endless belt 502a and a second carrier 500b including a second endless belt 502b. The first carrier 500a is positioned adjacent to the second carrier 500b to place the first surface 516a of the first endless belt 500a in contact with the first surface 516b of the second endless belt 500b. As discussed in more detail below, the arrangement shown in FIG. 15 defines a nip region 503 that extends in a curved or S-shaped path along the machine direction between the first endless belt 502a and the second endless belt 502b. The endless belts 502a, 502b are held against each other in the nip region 503 with an arrangement of tension rollers 521a, 521b that also allow the belts 502a, 502b to deflect away from each other by different amounts in the nip region 503 in accordance with the varying thicknesses of the substrate advancing through the nip region 503.

As shown in FIG. 15, the second surface 518a of the first endless belt 502a is in contact with the outer circumferential surface 523a of the tension rollers 521a in the nip region 503, and the second surface 518b of the second endless belt 502b is in contact with the outer circumferential surface 523b of tension rollers 521b in the nip region 503. The tension rollers 521a, 521b, which are adapted to rotate about respective axes of rotation 524, may be non-compliant or may be in the form of compliant rollers 520 discussed above. With continued reference to FIG. 15, the tension rollers 521a and the tension rollers 521b are positioned with respect to each other such portions of the first belt 502a and the second belt 502b both wrap partially around the outer circumferential surfaces 523a, 523b of the tension rollers 521a, 521b. As such, the first surface 516a of the first endless belt 500a is held in contact with the first surface 516b of the second endless belt 500b in the nip region 503. And the first and second endless belts 500a, 500b extend in a curved or S-shape in the machine direction through the nip region 503. Thus, tension rollers 521a, 521b exert opposing forces on the belts 502a, 502b toward each other to help hold the belts in contact with relatively thick and thin portions of the substrate advancing through the nip region 503.

Figure 17:
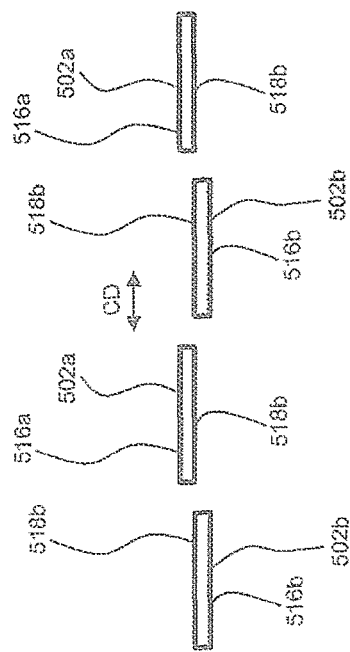
FIG. 17 is a detailed sectional view of the nip region of the compliant conveyance apparatus from FIG. 16 taken along line 17-17.
Figure 16:
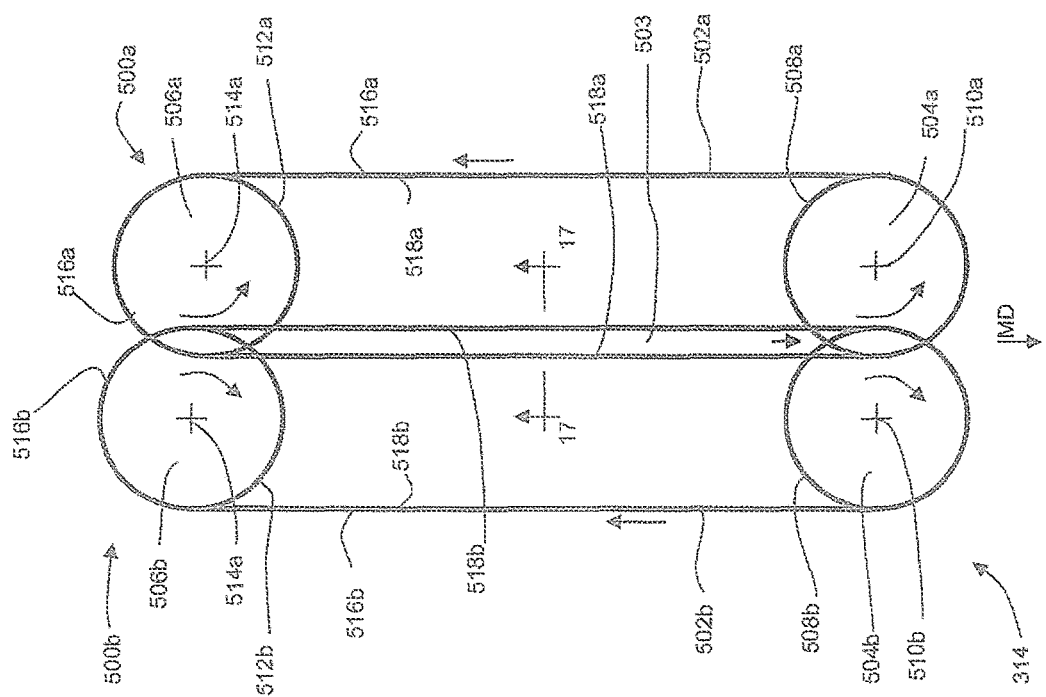
FIG. 16 is a side view of a fourth embodiment of a compliant conveyance apparatus.

FIG. 16 shows yet another configuration of a compliant conveyance apparatus 314 that includes a first carrier 500a with a plurality of first endless belts 502a and a second carrier 500b including a plurality of second endless belt 502b. Each of the first endless belts 502a are spaced apart from each other in the cross direction CD, and each of the second endless belts 502b are spaced apart from each other in cross direction CD. More particularly, the widths of the first endless belts 502a and second endless belts 502b are positioned in an alternating arrangement along the cross direction CD in the nip region 503. In addition, the first and second carriers 500a, 500b are positioned adjacent each other to create a relative interference positional relationship between the endless belts 502a, 502b in the nip region 503. More particularly, as shown in FIG. 17, the first and second carriers 500a, 500b are positioned to define a staggered elevation or position between planes defined by first surfaces 516a of the first endless belts 502a and planes defined by the first surfaces 516b of the second endless belts 502b. Thus, the relative staggered positions of the belts 502a, 502b help hold the belts in contact with relatively thick and thin portions of the substrate advancing through the nip region 503.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for conveying articles in a web converting process, the method comprising the steps of:
    providing a first carrier including a first plurality of compliant rollers in rolling contact with a first endless belt;
    providing a second carrier including a second plurality of compliant rollers in rolling contact with a second endless belt, wherein the first carrier is positioned adjacent the second carrier to define a nip region between the first endless belt and the second endless belt, the nip region having a length extending in a machine direction and a width extending in a cross direction, the first and second carriers being pre-loaded wherein the first plurality of compliant rollers and the second compliant rollers exert forces on the first endless belt and the second endless belt toward each other in the nip region;
    advancing a first continuous elastic laminate and a second continuous elastic laminate in the machine direction;
    providing a plurality of chassis, each chassis comprising a first end region and an opposing second end region separated from each other by a central region, and having a longitudinal axis and a lateral axis, the chassis comprising: a topsheet, a backsheet, and an absorbent core disposed between the topsheet and the backsheet;
    bonding the first end regions of each chassis with the first continuous elastic laminate, and bonding the second end regions of each chassis with the second continuous elastic laminate;
    folding each chassis along the lateral axis to position the first continuous elastic laminate into a facing relationship with the second continuous elastic laminate;
    bonding the first continuous elastic laminate with the second continuous elastic laminate at discrete bond regions before advancing the plurality of articles in the machine direction through the nip region to form a plurality of pant diapers connected with each other with the first and second continuous elastic laminates;

advancing the plurality of pant diapers in the machine direction through the nip region, each pant diaper having a varying thickness along the machine direction and the cross direction, the chassis corresponding with relatively thicker portions of the plurality of pant diapers, and the first and second continuous elastic laminates extending between the chassis corresponding with relatively thinner portions of the plurality of pant diapers;

deforming the compliant rollers to vary a distance between the first endless belt and the second endless belt along the machine direction and cross direction of the nip to conform with the varying thickness of the pant diapers, wherein the compliant rollers deform such that the first and second endless belts exert compression and frictional forces on the relatively thinner portions defined by the first and second continuous elastic laminates and the relatively thicker portions defined by the chassis advancing through the nip region; and cutting the first and second continuous elastic laminates in the cross direction to form discrete pant diapers after advancing the plurality of pant diapers through the nip region.

2. The method of claim 1, wherein the step of varying a distance further comprises deforming at least one of the first plurality of rollers.

3. The method of claim 2, wherein each roller of the first plurality of rollers includes a hub member, a rim member surrounding the hub member, and an intermediate member connecting the hub member with the rim member.

4. The method of claim 3, wherein the step of varying the distance between the first belt and the second belt includes deforming rim members and intermediate members of rollers.

5. The method of claim 3, wherein the intermediate member comprises a plurality of spokes members, and wherein the step of varying the distance between the first belt and the second belt includes bending spoke members.

6. The method of claim 3, wherein each roller of the second plurality of rollers includes a hub member, a rim member surrounding the hub member, and an intermediate member connecting the hub member with the rim member.

7. The method of claim 6, wherein the step of varying the distance between the first belt and the second belt includes deforming rim members of the first and second pluralities of rollers.

8. The method of claim 7, wherein the step of varying the distance between the first belt and the second belt includes bending intermediate members of the first and second pluralities of rollers.

\* \* \* \* \*